United States Patent [19]
Shrive et al.

[11] Patent Number: 5,463,902
[45] Date of Patent: Nov. 7, 1995

[54] SOFT TISSUE EXTENSOMETER

[75] Inventors: Nigel G. Shrive; Erich Damson, both of Calgary, Canada; Richard A. Meyer, Carver; Scott P. Iverslie, Chanhassen, both of Minn.

[73] Assignee: University Technologies International Inc., Canada

[21] Appl. No.: 112,841

[22] Filed: Aug. 27, 1993

[51] Int. Cl.$^6$ .................................................. G01B 5/30
[52] U.S. Cl. ................................................ 73/781; 33/790
[58] Field of Search ........................... 73/781, 826, 831, 73/178, 779; 33/783, 784, 787–790, DIG. 13

[56] References Cited

U.S. PATENT DOCUMENTS

| | | | |
|---|---|---|---|
| 2,416,664 | 2/1947 | Ruge | 33/790 |
| 2,681,566 | 6/1954 | Ruge | 33/787 |
| 2,917,920 | 12/1959 | Robinette et al. | 73/95 |
| 3,319,338 | 5/1967 | Nicola | 33/148 |
| 3,514,864 | 6/1970 | Davidson et al. | 33/787 |
| 3,937,212 | 2/1976 | Fletcher et al. | 128/2 |
| 4,141,345 | 2/1979 | Allen et al. | 128/2 |
| 4,223,443 | 9/1980 | Bachmann et al. | 33/148 |
| 4,249,417 | 2/1981 | Feldstein et al. | 73/141 |
| 4,294,015 | 10/1981 | Drouin et al. | 33/174 |
| 4,823,473 | 4/1989 | McMahon | 33/787 |
| 5,083,465 | 1/1992 | Myers | 33/790 |
| 5,123,175 | 6/1992 | van der Kuur | 33/789 |
| 5,377,553 | 1/1995 | Knepper, Jr. | |

FOREIGN PATENT DOCUMENTS

| | | | |
|---|---|---|---|
| 1084938 | 7/1960 | Germany | 73/826 |
| 2132374 | 11/1988 | Japan. | |
| 1145-268-A | 7/1982 | U.S.S.R. | |
| 289203 | 4/1928 | United Kingdom | 33/788 |

OTHER PUBLICATIONS

"Miniature Force Transducer for Myocardial Stimulation and Local Tension Measurements" by Y. Hasin et al., *EEE Transactions on Biomedical Engineering*, vol. BME–26, No. 2, Feb. 1979.

Product Announcement and Application Notes for MTS Extensometer–Model 632.53.

Product Announcement for MTS Extensometer–Model 632.54.

Products Specification for MTS Model 632.59 High–Temperature Axial Extensometer.

Application Notes for MTS Very High Temperature Axial Extensometer–Model 632.59.

*Primary Examiner*—R. Raevis
*Attorney, Agent, or Firm*—Westman, Champlin & Kelly

[57] ABSTRACT

An extensometer for measuring strain in a test specimen is disclosed. The extensometer includes a frame and a flexible support structure, preferably, a loop, mounted to the frame. A measuring device is mounted to the flexible support loop at a position spaced apart from the frame and engages a surface of the specimen with a selected amount of contact force. The measuring device provides an output signal proportional to the measured strain.

16 Claims, 3 Drawing Sheets

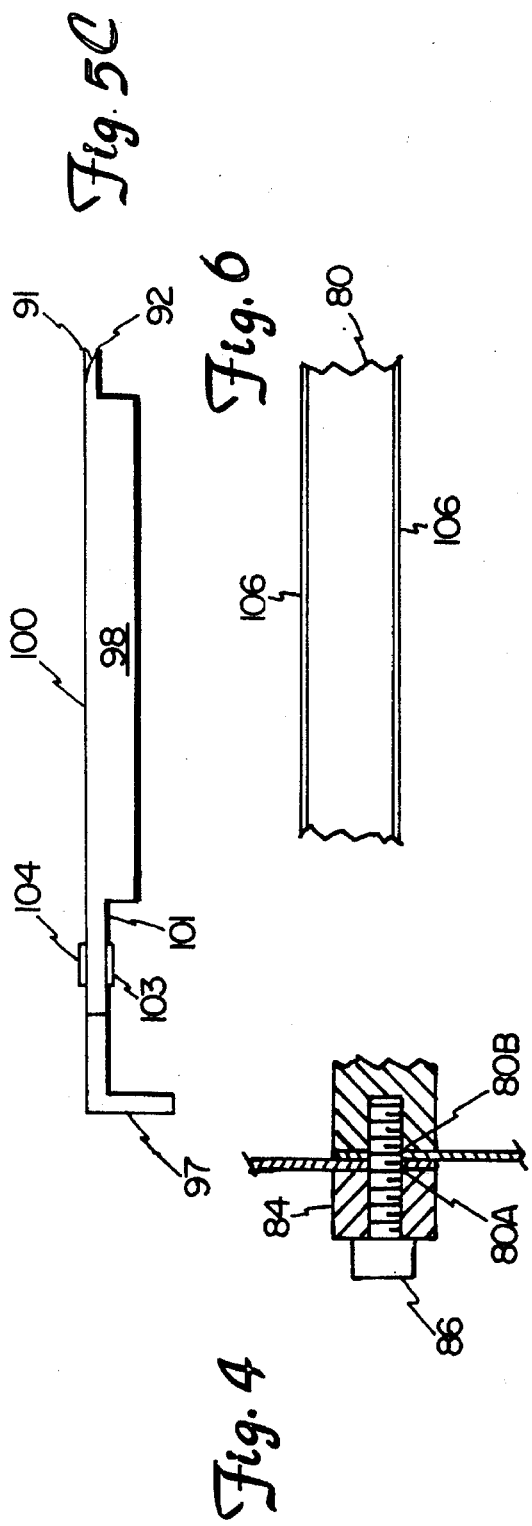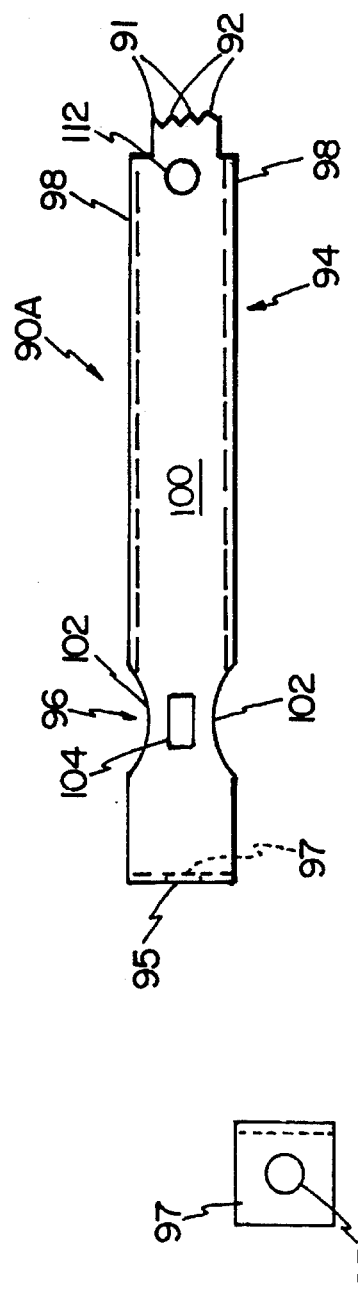

SOFT TISSUE EXTENSOMETER

BACKGROUND OF THE INVENTION

The present invention relates to extensometers used to measure strain in a specimen. More particularly, the present invention provides an extensometer with low contact forces upon the test specimen enabling it to be used on soft or friable materials or tissues.

Measurement of strain in soft materials such as biological tissues or friable materials is a desired yet difficult procedure. Extensometers, which measure the strain in the tissue by measuring deformation, are well known in the art. Standard spring-loaded knife-edge extensometers although quite useful with harder materials such as metal are not suitable since these extensometers may cut the surface of the test specimen thereby influencing the test results. Likewise, strain gages mounted directly to the test specimen are also not suitable even if a glue could be found which did not react with the tissue since mere adhesion of the strain gage to the tissue alters the strain characteristics of the tissue.

Optical based systems wherein contact is not made directly with the test specimen, but rather, by measuring displacement of markers such as dyelines painted onto the surface of the tissue, have been advanced. Although these systems have the advantage of being contactless with the test specimen, the system has some disadvantages. For instance, these systems first require precise positioning of the camera to monitor the markers. Secondly, since the camera sees only a planar view of the test specimen, mere rotation or realignment of the specimen during the test can appear as strain or movement of the markers when actually no strain has occurred.

SUMMARY OF THE INVENTION

An extensometer for measuring strain in a test specimen, particularly a soft tissue specimen, is disclosed. The extensometer includes a frame and a flexible support structure, preferably, a support loop, mounted to the frame. A measuring device is mounted to the flexible support loop at a position spaced apart from the frame and engages a surface of the specimen with a selected amount of contact force. The measuring device provides an output signal proportional to the measured strain in the test specimen as measured directly by its deformation.

In the embodiment described, the flexible support loop comprises an endless loop formed from a flexible strap having a first end and a second end. The first end and the second end are mounted to the frame, while the measuring device is mounted to the flexible support loop between the first and the second ends. With contact of the measuring device upon the surface of the specimen, the amount of contact force can be accurately adjusted by compressing the flexible support loop. Since the loop is the only structure supporting the measuring device against the test specimen, and since the loop is flexible, the support loop allows for three-dimensional movement of the specimen without inducing large resistive forces which could distort the test specimen or cause the measuring device to slip on the test specimen. The support loop further allows the measuring device to move with the test specimen when the test specimen is undergoing "rigid body" displacements. Measuring strain as the change in length of two contact points, the accuracy of test results is increased since common mode displacement of the contact points is compensated for by the support loop.

In a preferred embodiment, the frame includes a support arm having a longitudinal slot. The flexible support loop is mounted to a hinge assembly which in turn is mounted to the support arm using the longitudinal slot. Movement of the support arm adjusts the compression of the flexible support loop and thereby the amount of contact force. Pivotal movement of the hinge assembly provides an uplifting force upon a portion of the support loop to compensate for the weight of the measuring device and thus support the measuring device.

In a further preferred embodiment, the measuring device comprises two extensometer arms that are spaced apart and generally parallel to each other. A first end of each arm is joined to the flexible support loop, while a second end of each arm contacts the surface of the specimen. Each arm includes a rigid body portion that resists bending and a flexible body portion which is substantially compliant. Strain sensors mounted on the flexible body portion provide an output signal proportional to the strain in the test specimen upon displacement of the extensometer arms from each other due to specimen loading. Spaced apart contact points are provided on each arm to distribute the contact force upon the test specimen to prevent cutting and slipping. Preferably, the contact points comprise tips that extend from the major planar surface of each arm in alternating orientation.

In yet another preferred embodiment, the extensometer includes an aligning device to locate the measuring device to a preselected calibrated position. The aligning device is frictionless or contactless to insure that the aligning device follows and does not inhibit the freebody motion of the test specimen. In the embodiment described the aligning device includes an aligning pin mounted to the measuring device and an aligning rod extending from the frame toward the aligning pin wherein the preselected position is obtained upon alignment of the pin with the rod. Alignment of the measuring device to the test specimen is made with adjustments provided on the frame which include rotation of the hinge assembly.

The present invention provides an extensometer well suited for use on soft materials where low contact three is not only desired but required. The low contact force insures that the material will not be cut by engagement with the measuring device. Use of the flexible support loop insures accurate tracking of the measuring device upon the test specimen minimizing common mode error, while the aligning device allows the test conditions to be accurately applied over a run of tests.

BRIEF DESCRIPTION OF THE DRAWINGS

FIG. 4 is a sectional view taken as on line 4—4 of FIG. 2;

FIG. 5A is a top plan view of an extensometer arm;

FIG. 5B is a side elevational view of the extensometer arm of FIG. 5A;

FIG. 5C is a side elevational view of the extensometer arm of FIG. 5A; and

FIG. 6 is a partial top plan view of a flexible strap.

DETAILED DESCRIPTION OF THE PREFERRED EMBODIMENTS

Figure 1:
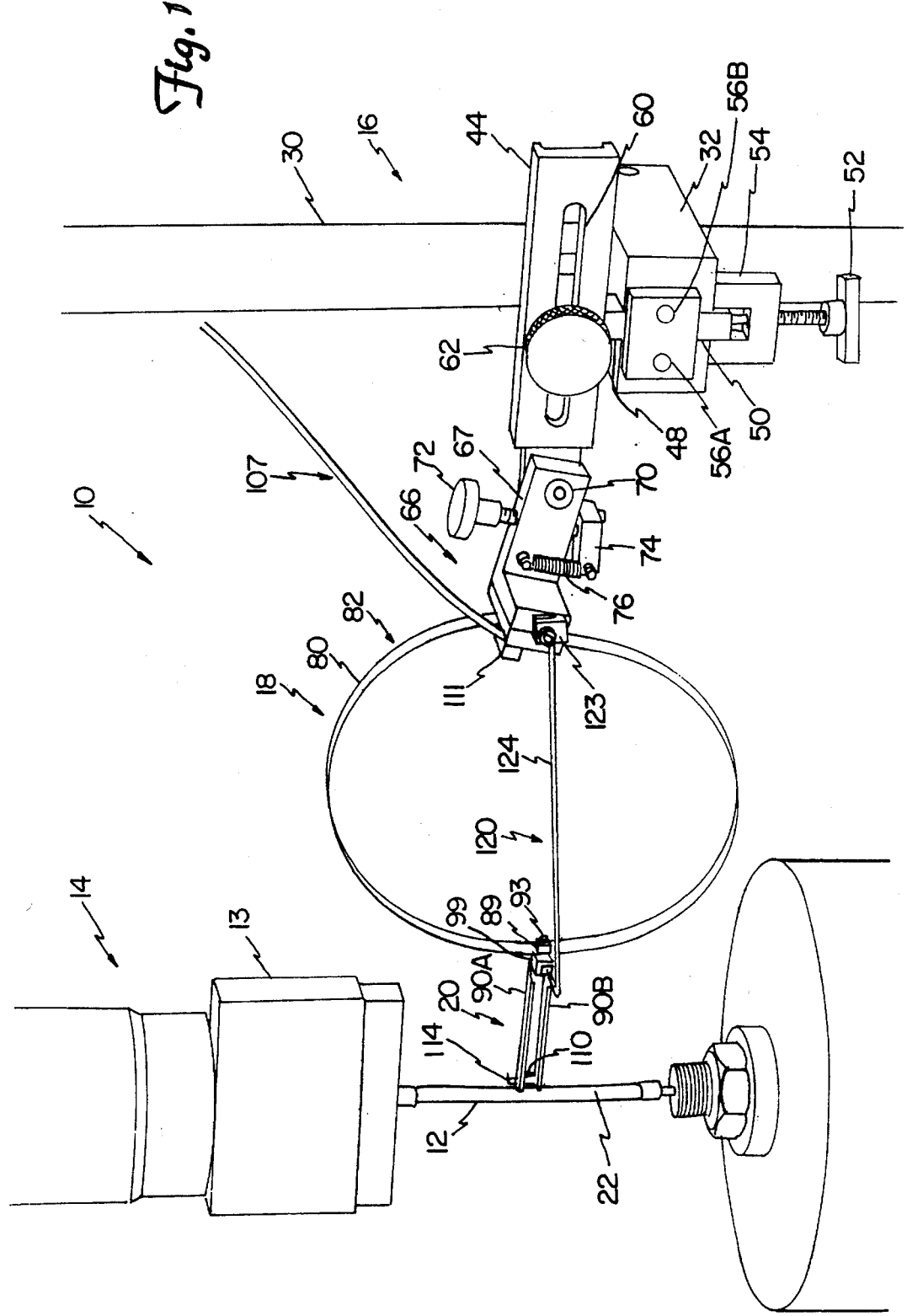
FIG. 1 is a perspective view of an extensometer of the present invention with parts broken away.
Figure 2:
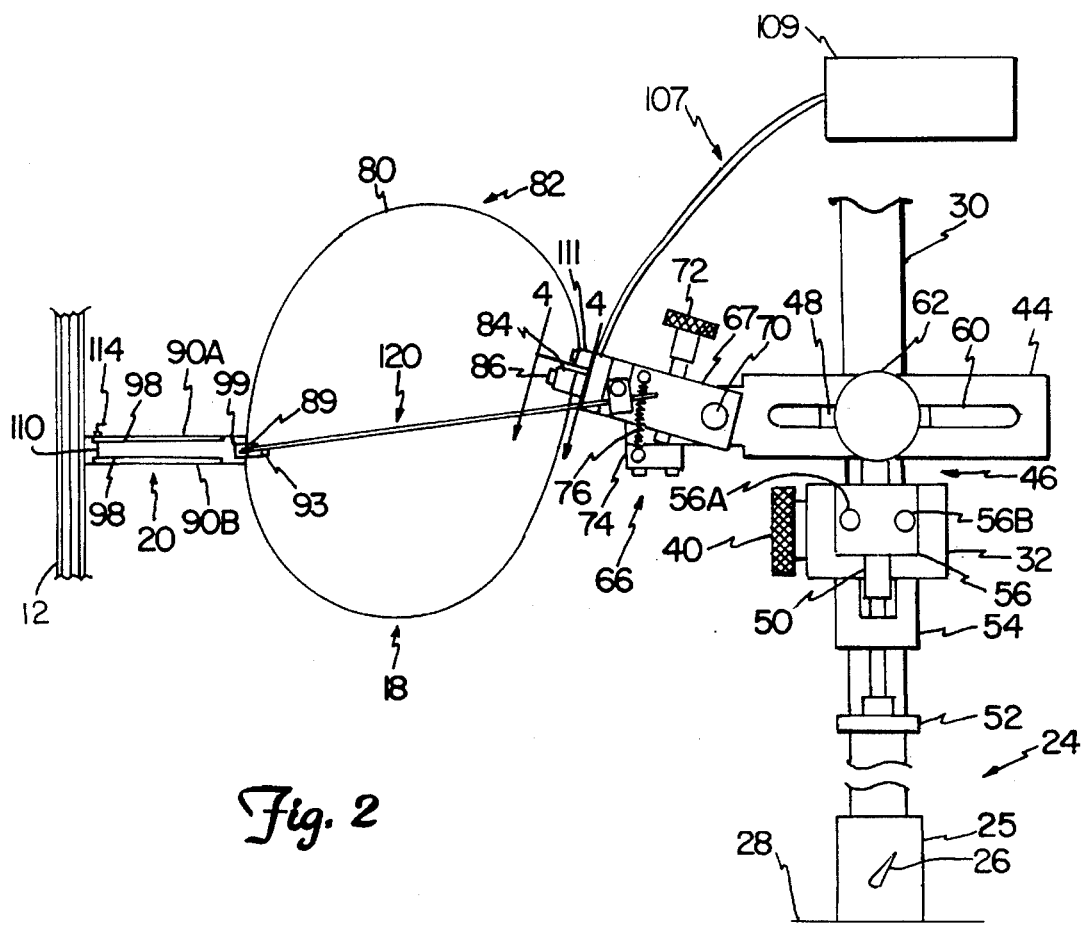
FIG. 2 is a side elevational view of the extensometer with parts broken away.
Figure 3:
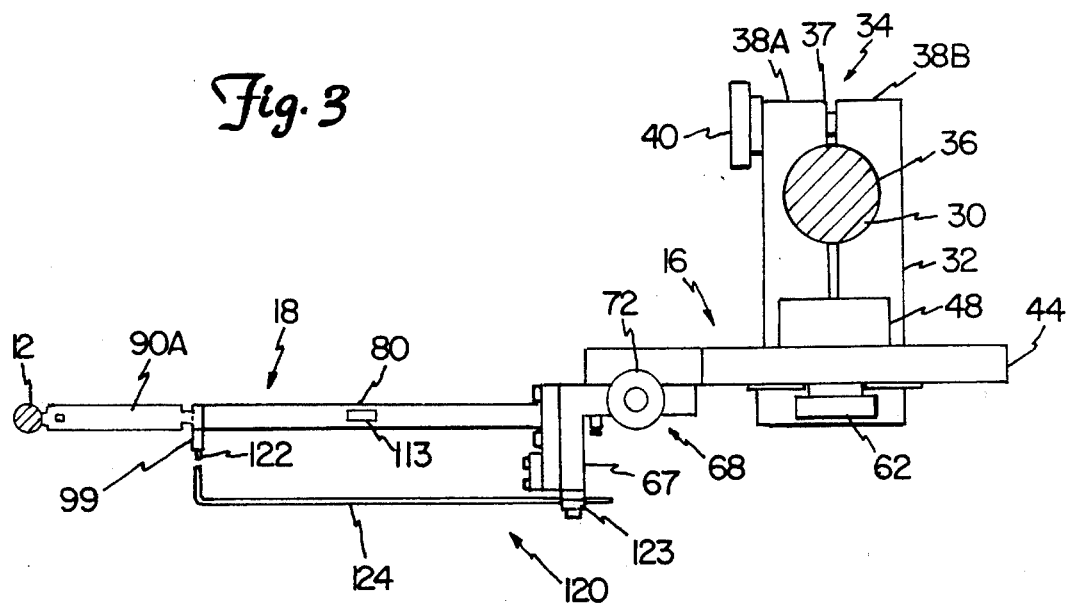
FIG. 3 is a top plan view of the extensometer.

FIGS. 1–3 illustrate an extensometer 10 of the present invention. The extensometer 10 measures strain in a specimen 12 when the specimen 12 is subjected to loading from a loading apparatus 14, the amount of load applied being measured by a suitable transducer 13. Generally, the extensometer 10 includes a frame 16, a flexible support structure 18 and a strain measuring device 20. The strain measuring device 20 contacts a surface 22 of the specimen 12. As illustrated, the flexible support structure 18 supports the strain measuring device 20 on the frame 16 and against the specimen 12, preferably providing low contact force upon the surface 22.

Referring to each of the major components of the extensometer 10 in detail, the frame 16 includes a support base 24. Preferably, the support base 24 comprises a base stand 25 having a magnet, not shown. Using a switch 26, the magnet is selectively positioned near a support table 28 to provide a stable foundation.

A support rod 30 extends upwardly from the base 24. A support block 32 includes a clamping device 34 through which the support block 32 can be selectively positioned along an axis of the support rod 30. The clamping device 34 includes an aperture 36 provided in the support block 32. A slot 37 extending from an edge of the support block 32 and through the aperture 36 forms two bendable arms 38A and 38B. A thumbscrew 40 extending through an aperture in the arm 38A and threaded into a suitable aperture in arm 38B allows the support block 32 to be selectively clamped to the rod 30.

A support arm 44 is mounted to the support block 32 through an adjustment mechanism 46. With the support block 32 fixed to the rod 30, the adjustment mechanism 46 allows accurate positioning of the support arm 44 relative to the axis of the rod 30. The adjustment mechanism 46 includes a T-bracket 48 slidably located in a channel 50 of the support block 32. A thumbscrew 52 threaded through a suitable aperture in a U-shaped bracket 54 attached to the support block 32 bears against an end of the T-bracket 48 to adjust its position relative to the channel 50. A locking plate 56 insures that the T-bracket 48 is held securely in a fixed position within the channel 50 when the screws 56A and 56B are tightened.

In the embodiment illustrated the support arm 44 includes a slot 60 to allow movement of the support arm 44 relative to the support rod 30. A thumbscrew 62 extending through the slot 60 and threaded in a suitable aperture in the T-bracket 48 allows the support arm 44 to be adjustably fixed to the T-bracket 48 in a direction generally perpendicular to the axis of the support rod 30.

The flexible support structure 18 is attached to the frame 16 and specifically to the support arm 44 preferably using a hinge assembly 66. The hinge assembly 66 allows fine adjustment of the support structure 18 relative to the frame 16 in order to adjust the measuring device 20 relative to the specimen 12. The hinge assembly 66 includes a bracket 67 pivotally joined to the support arm 44 with a pivot pin 70. A thumbscrew 72 threaded through a suitable aperture in the bracket 67 contacts an arm 74 of the support arm 44. Adjustment of the thumbscrew 72 allows the angular position of the bracket 67 to be adjusted relative to the support arm 44. In the embodiment illustrated, a spring 76 connected between the bracket 67 and the support arm 74 provides a restraining force to assure that the angular position of the bracket 67 is suitably fixed.

As stated above, the flexible support structure 18 supports the measuring device 20 against the specimen 12 and on the frame 16. In the embodiment illustrated, the flexible support structure 18 comprises a flexible strap 80 (FIG. 6) formed of beryllium-nickel. Preferably the strap 80 is formed in the shape of a loop 82 with ends of the strap joined together and clamped to the bracket 67 with a clamping plate 84. Referring to FIG. 4, each end of the strap 80 is provided with an aperture 80A and 80B, respectively. The ends of the strap 80 are then overlapped aligning the apertures 80A and 80B with each other. A mounting bolt 86 which extends through the clamping block 84 and the apertures 80A and 80B of the ends of the strap 80 secures the ends of the strap 80 to provide an enclosed loop 82. It is to be understood that the ends of the strap 80 could also be welded together to form an endless enclosed loop and then secured to the bracket 67 through suitable means. Likewise, the loop 82 formed by the strap 80 could be non-continuous in that the ends of the strap 80 could be spaced apart and separately mounted to the bracket 67. The important feature of the support structure 18 is that it independently provides support for the measuring device 20 placing the measuring device 20 in a proper position against the specimen 12. Since the strap 80 is flexible, the support loop 82 allows for three-dimensional movement of the test specimen 12 without inducing large resistive forces which could distort the test specimen 12. The support loop 82 further allows the measuring device 20 to move with the test specimen 12 when the test specimen is undergoing common mode displacements of the contact points on the test specimen 12. When compressed slightly by adjustment of the support arm 44 relative to the T-bracket 48, the support loop 82 provides an adjustable amount of contact force.

In the embodiment illustrated the measuring device 20 includes two extensometer arms 90A and 90B. The arms 90A and 90B are substantially similar and include a first end mounted to the flexible support structure 18 with a screw 93 extending through a mounting block 89, an aperture, not shown, in the strap 80, an aperture 95 in each arm of an extending tab 97 (FIG. 5B) and threaded in a backing block 99. A second end of each arm 90A and 90B contacts the surface 22 of the specimen 12 with the contact force developed by the flexible support structure 18. Pivotal rotation of the hinge assembly 66 provides an uplifting force upon the measuring device 20 for support thereof as well as distributes the contact three between each of the arms 90A and 90B so that the force from each arm upon the test specimen 12 is substantially equal. Substantially equal force contact from each arm is desired in order to minimize the total contact force applied to the test specimen 12. For instance, if the contact forces from each arm were not equal and if a minimum contact force was required to prevent slipping, then in order to maintain the arm with the lesser amount of contact force at the minimun amount of contact force, the other arm would be applying a higher, unnecessary amount of force, which could distort the test specimen 12 affecting test results.

It is important to understand that the adjustments made through thumbscrews 40, 52, 62 and 72, which allow the measuring device 20 to be aligned with the test specimen 12, and which allow the total amount of contact force applied to the test specimen 12 to be adjusted, as well as the amount of contact force applied through each extensometer arm 90A and 90B to be adjusted in effect adjust the position of mounting block 84 and thus the mounting point of the flexible support structure 18 relative to a stationary reference point. Other adjustable mounting arrangements are possible to accomplish this purpose. For instance, the flexible support structure 18 could be mounted to the support block 32 with a rigid support arm in other words without the hinge assembly 66. Likewise, the length of the support arm from the axis of the rod 30 could be fixed by removing the slot 60. Adjustment of the total contact force translational movement of the mounting block 84 and thus the mounting point of the flexible support structure 18 could then be accomplished by either adjusting the position of the base 25 on the table surface 28, or by suitable means to move the rod 30 relative to the base 25. Similarly, alignment of the measuring device 20 with the test specimen 12 through pivotal movement of the mounting block 84 could be accomplished with a suitable hinge assembly mounting the rod 30 to the base 25 thereby allowing the rod 25 to tilt in a manner similar to pivotal movement of the bracket 67.

Referring to FIG. 5A wherein extension arm 90A is illustrated by way of example, preferably, the ends of the extensometer arms 90A and 90B include spaced apart contact points or tips 91 and 92 so that the contact force is distributed upon the surface 22 in order that the specimen 12 is not cut and that the extensometer arms 90A and 90B do not slip on the surface 22. As illustrated in FIG. 5C, the plurality of contact points indicated at 91 are preferably turned upwardly away from an upper major planar surface 100, while the plurality of contact points 92 are preferably turned downwardly from a lower major planar surface 101. Referring back to FIG. 5A, orientation of the contact points 91 and 92 alternates across the width of the extension arm.

Generally, each extensometer arm is made of beryllium-nickel and includes a substantially rigid body portion 94 that resists bending and a flexible body portion 96 that is substantially compliant and bends with movement of the arm. The rigid body portion 94 is formed by parallel side walls 98 extending from the planar surface 101 to provide a U-shaped channel. The flexible body portion 96 is connected to the rigid body portion 94 on an end remote from the plurality of contact points 91 and 92. Recesses 102 formed inwardly from the side edges of the planar surfaces 100 and 101 make the extensometer compliant in the flexible body portion 96. Suitable strain sensors, two of which are illustrated as 103 and 104, mounted to the upper and lower surfaces of each of the flexible body portions of each extensometer arm 90A and 90B together provide an output signal proportional to the change in length of the contact points of each arm away from each other, and thus, is proportional to the strain in the test specimen 12. Preferably, the strain sensors are connected in a conventional Wheatstone bridge circuit with excitation and output signals to and from the measuring device 20 provided on conductive traces, two of which are illustrated as 106 in FIG. 6, provided on the flexible strap 80. Signal lines, generally illustrated at 107, from a power supply and recording device 109 are electrically connected to the conductive traces 106 and thus to the measuring device 20. A cable clamp 111 secures the signal lines 107 to the bracket 67.

Referring back to FIG. 2, an overtravel stop 110 is provided to limit movement of the arms 90A and 90B away from each other. The overtravel stop 110 is fastened to the upper surface of the lower arm 90B between side walls 98 thereof and extends upwardly through an aperture 112 provided in the upper arm 90A (FIG. 5A). Travel of the arms 90A and 90B is limited with contact of the upper arm 90A upon an extending flange 114 of the overtravel stop 112.

In the embodiment illustrated the extensometer 10 further includes an aligning device 120 to locate the measuring device 20 to a preselected calibrated position. Preferably, the aligning device 120 is frictionless or contactless to insure that the aligning device 120 does not affect the preselected position. As illustrated in FIG. 3, the aligning device 120 includes an aligning pin 122 extending outwardly from the backing block 99 and an aligning rod 124 extending from a rod clamp 123 mounted to the bracket 67 toward the aligning pin 122 wherein the preselected position is obtained upon alignment of the pin 122 with the rod 124. Alignment of the measuring device 20 with the specimen 12 is made with adjustments provided on the frame 16 which include rotation of the hinge assembly 66 with the thumbscrew 72. When the desired position of the measuring device 20 with respect to the test specimen 12 has been obtained with the desired contact force, the remote end of the rod 124 is positioned proximate the pin 122 by adjusting the rod clamp 123.

For optimal extensometer operation, the extensometer 10 must be balanced and aligned before engagement with the test specimen 12. Preferably, it is best to do the balancing on a suitable calibrator, which will measure the amount of contact force, but it can also be done with a dummy specimen. The goal is to operate the extensometer in exactly the same position during testing, as it was balanced in during setup.

The setup procedure is as follows:

First, determine the contact force to be used for the test. For low contact force applications (less than four grams per contact), the hinge assembly 66 must be rotated to compensate for the weight of the measuring device 20. This is done by turning the thumbscrew 72, allowing the hinge assembly 66 to rotate until the extensometer arms 90A and 90B are parallel to the table surface 28 when in the free position. For soft tissue, a contact force in the order of one gram is sufficient for full, non-slip contact.

With the extensometer arms 90A and 90B in position, bring the extensometer arms 90A and 90B into engagement with the dummy specimen. Then, using a suitable spring scale, not shown, measure the contact force by placing a suitable portion of the spring scale sensor in front of the overtravel stop 110 and pulling the measuring device 20 away from the test specimen 12 and against the spring force of the flexible support structure 18 until contact is no longer made with the test specimen 12. Movement of the support arm 44 in or out adjusts the amount of contact force. If desired, strain sensors, one of which is shown in FIG. 3 at 113, can be mounted to the flexible support loop 82 to measure the compression of the flexible support loop and provide an output signal proportional to the force contact upon the specimen 12.

Vertically adjust the position of the measuring device 20 with the thumbscrew 52, and if necessary the clamping assembly 34, until both extensometer arms 90A and 90B contact the test specimen 12 with the same force. Proper alignment of the extensometer arms 90A and 90B with the hinge assembly 66 should insure that each arm applies the same amount of force. In other words, all of the contact force should not be just through the upper extensometer arm 90A nor through just the lower extensometer arm 90B, but rather, through each arm equally. As illustrated in FIG. 2, the extensometer arms 90A and 90B will be below the center line of the hinge assembly 66 when properly positioned.

The aligning device 120 allows this operating position to be repeated when desired. In the embodiment illustrated, loosen the rod clamp 123 and adjust the rod 124 until the remote end of the rod 124 is aligned with the pin 122. Tighten the rod clamp 123 making sure that the pin 122 and the end of the rod 124 remain aligned with each other.

Removal of the measuring device 20 from the test specimen 12 allows the flexible support structure 18 to expand; however, when another test specimen 12 is brought into contact with the measuring device 20, the extensometer 10 can be quickly adjusted to its preselected calibrated position as determined when the pin 122 and the rod 124 are aligned.

In summary, the present invention provides an extensometer well suited for use on test specimens where low, repeatable contact force is desired. The low contact force insures that the material will not be cut by engagement with the measuring device. Use of a flexible support structure to fully support the measuring device in contact with the test specimen minimizes the force applied to the test specimen, while insuring accurate tracking of the measuring device upon the test specimen to reduce common mode error. An aligning device is optionally included that allows the test conditions to be accurately applied over a run of tests.

Although the present invention has been described with reference to preferred embodiments, workers skilled in the art will recognize that changes may be made in form and detail without departing from the spirit and scope of the invention.

What is claimed is:

1. An extensometer for measuring strain in a specimen, the extensometer comprising:

a flexible support loop a pair of arms mounted to the flexible support loop, each arm having an end that is engagable with a portion of a surface of the specimen with an amount of contact force so as to move with the corresponding portion and provide an indication as to the strain in the specimen;

a frame joined to the flexible support loop at a position spaced apart from the pair of arms, the frame supporting the flexible support loop and the pair of arms and being adjustably securable to a stationary support surface so as to compress the flexible support loop and generate the contact force.

2. The extensometer of claim 1 wherein the flexible support loop comprises an endless loop.

3. The extensometer of claim 1 wherein the flexible support loop includes a first end and a second end.

4. The extensometer of claim 3 wherein the first end and the second end are mounted to the frame.

5. The extensometer of claim 1 wherein each arm has a second end remote from each corresponding first-mentioned end, and wherein the second ends are joined to the flexible support loop.

6. The extensometer of claim 5 wherein each arm includes a rigid body portion and a flexible body portion and wherein a strain sensor is mounted to each of the flexible body portions and operably connected together for providing an output signal proportional to the strain in the specimen.

7. The extensometer of claim 5 wherein each of the first-mentioned ends includes a first contact point engaging the specimen and extending in a first direction from the corresponding arm, and a second contact point engaging the specimen at a position spaced apart from the first contact point, the second contact point extending from the corresponding arm in a second direction.

8. The extensometer of claim 1 and further comprising a conductive path joined to the flexible support loop for transmitting the output signal.

9. The extensometer of claim 8 wherein the output signal is an electrical signal and the conductive path comprises electrically conductive traces formed on the flexible support loop.

10. The extensometer of claim 1 and further comprising a support arm secured to the flexible support loop and adjustably secured to the frame.

11. The extensometer of claim 10 wherein the support arm is pivotable on the frame for allowing pivotal movement of a portion of the flexible support loop.

12. The extensometer of claim 1 and further comprising aligning means for aligning the pair of arms relative to the frame.

13. The extensometer of claim 1 and further comprising a pair of contactless aligning members wherein a first member is mounted to the frame and a second member is mounted to the flexible support loop.

14. The extensometer of claim 13 wherein the second member comprises a pin and the first member comprises a rod extending toward the pin.

15. An extensometer for measuring strain in a specimen, the extensometer comprising:

a first extensometer arm having a first end for engaging a first portion of a surface of the specimen;

a second extensometer arm having a second end for engaging a second portion of the surface of the specimen wherein displacement of the first end and the second end provide an indication as to the strain in the specimen; and wherein each end of each extensometer arm includes a first contact point engaging the specimen and extending in a first direction from a reference planar surface, and a second contact point engaging the specimen and extending in a second direction from the reference planar surface so that the first contact point and the second contact point are on opposite sides of the reference planar surface.

16. The extensometer of claim 15 wherein each extensometer arm includes a third contact point engaging the specimen and extending in the first direction from the reference planar surface, the second contact point being located between the first and third contact points.

* * * * *